US012629333B2

(12) United States Patent
Müller et al.

(10) Patent No.: US 12,629,333 B2
(45) Date of Patent: May 19, 2026

(54) ORAL THIN FILM

(71) Applicant: LTS LOHMANN THERAPIE-SYSTEME AG, Andernach (DE)

(72) Inventors: Markus Müller, Troisdorf (DE); Michael Linn, Waldböckelheim (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 1070 days.

(21) Appl. No.: 17/621,147

(22) PCT Filed: Jul. 2, 2020

(86) PCT No.: PCT/EP2020/068598
§ 371 (c)(1),
(2) Date: Dec. 20, 2021

(87) PCT Pub. No.: WO2021/001461
PCT Pub. Date: Jan. 7, 2021

(65) Prior Publication Data
US 2022/0347090 A1      Nov. 3, 2022

(30) Foreign Application Priority Data

Jul. 2, 2019      (DE) ..................... 10 2019 117 870.3

(51) Int. Cl.
| | |
|---|---|
| *A61K 9/00* | (2006.01) |
| *A61K 9/70* | (2006.01) |
| *A61K 31/135* | (2006.01) |
| *A61K 31/137* | (2006.01) |
| *A61K 47/02* | (2006.01) |
| *A61K 47/38* | (2006.01) |

(52) U.S. Cl.
CPC ............ *A61K 9/006* (2013.01); *A61K 31/135* (2013.01); *A61K 47/02* (2013.01); *A61K 47/38* (2013.01)

(58) Field of Classification Search
CPC ...... A61K 9/006; A61K 31/135; A61K 47/02; A61K 47/38
See application file for complete search history.

(56) References Cited

U.S. PATENT DOCUMENTS

| | | | | |
|---|---|---|---|---|
| 3,972,995 | A * | 8/1976 | Tsuk ........................ | A61K 9/70 424/435 |
| 5,154,929 | A | 10/1992 | Shibata et al. | |
| 8,741,918 | B2 * | 6/2014 | Cincotta ................ | A61K 31/00 514/288 |
| 9,095,577 | B2 | 8/2015 | Myers et al. | |
| 2012/0213912 | A1 | 8/2012 | Leonhard et al. | |
| 2020/0038936 | A1 * | 2/2020 | Dong ........................ | B21K 1/38 |
| 2020/0383936 | A1 | 12/2020 | Schmitz et al. | |

FOREIGN PATENT DOCUMENTS

| | | | | |
|---|---|---|---|---|
| BR | 112016008356-3 A2 | 8/2017 | | |
| DE | 3911699 C2 | 4/1998 | | |
| DE | 102017129012 A1 * | 6/2019 | ........... | A61K 31/135 |
| WO | 2010012437 A1 | 2/2010 | | |
| WO | 2011057714 A2 | 5/2011 | | |
| WO | 2014020155 A1 | 2/2014 | | |
| WO | 2015083181 A2 | 6/2015 | | |

OTHER PUBLICATIONS

German Office Action on Application No. 10 2019 117 870.3, dated Jun. 25, 2020, 10 pages.
International Preliminary Examination Report on Application No. PCT/EP2020/068598, dated Dec. 11, 2020, 6 pages.
International Search Report for Application No. PCT/EP2020,068598, dated Sep. 7, 2020, 12 pages.
Third Party Observation for Brazilian Patent Application No. 112021025586-9, dated Sep. 26, 2024.

* cited by examiner

*Primary Examiner* — Michael P Cohen
(74) *Attorney, Agent, or Firm* — Lippes Mathias LLP

(57)      ABSTRACT

The present invention relates to an oral thin film comprising at least one polymer and at least one pharmaceutically active agent, wherein the concentration of the at least one pharmaceutically active agent in the oral thin film is greater than the saturation concentration of the at least one pharmaceutically active agent in the oral thin film, and wherein the oral thin film comprises at least one material which serves as crystal nucleus for the at least one pharmaceutically active agent, to a method for producing said oral thin film, and to the use of said oral thin film as a medicament.

17 Claims, 1 Drawing Sheet

ORAL THIN FILM

The present invention relates to an oral thin film, a method for production thereof, and use thereof as a medicament.

Oral thin films (OTFs) are thin films containing at least one pharmaceutically active agent that are placed directly in the oral cavity or against the oral mucosa and dissolve there. These films are, especially, thin active agent-containing polymer-based films which, when applied to a mucous membrane, especially the oral mucosa, deliver the active agent directly into same. The very good blood supply to the oral mucosa ensures a rapid transfer of the active agent into the bloodstream. This dosage system has the advantage that the active agent is resorbed for the most part by the mucous membrane, thus avoiding the first-pass effect, which occurs in the case of the conventional dosage form of an active agent in tablet form. The active agent may be dissolved, emulsified or dispersed in the film.

Oral thin films known from the prior art have the disadvantage that the amount of the at least one pharmaceutically active agent contained therein is limited substantially by the saturation concentration of the at least one pharmaceutically active agent in the oral thin film. Attempts have also been made, however, to provide oral thin films which contain the at least one pharmaceutically active agent in a concentration that is greater than the saturation concentration of the at least one pharmaceutically active agent in the oral thin film. In oral thin films of this kind, however, the active agent is present substantially in undissolved form, and therefore these oral thin films are also known as suspension OTFs. These suspension OTFs, however, have the disadvantage that the active agent can crystallise in an uncontrolled and inhomogeneous manner during the compound production, the coating and/or the drying of the oral thin film and can thus lead to inhomogeneous active agent laminates insofar as the active agent is present in the coating compound in (partially) dissolved form. These inhomogeneous active agent laminates are disadvantageous in many respects. Their mechanical integrity can thus be reduced by the inhomogeneous crystallisation of the active agent, and the bioavailability of the active agent can be adversely affected by the inhomogeneous crystallisation of the active agent.

For example, WO 2014/020155 A1 discloses an OTF based on a solid suspension.

The aim of the present invention lies in overcoming the above-mentioned disadvantages of the prior art. Especially, the aim of the present invention lies in providing an oral thin film having a relatively high active agent content, i.e. an active agent concentration that is greater than the saturation concentration of the at least one pharmaceutically active agent in the oral thin film, at which the at least one pharmaceutically active agent does not crystallise inhomogeneously, but is present in the oral thin film as a substantially homogeneous crystal phase. In addition, a further object of the present invention lies in providing an economically acceptable method for producing such an oral thin film.

The above aim is addressed by an oral thin film according to claim 1 which comprises at least one polymer and at least one pharmaceutically active agent, wherein the concentration of the at least one pharmaceutically active agent in the oral thin film is greater than the saturation concentration of the at least one pharmaceutically active agent in the oral thin film, and wherein the oral thin film comprises at least one material which serves as crystal nucleus for the at least one pharmaceutically active agent.

An oral thin film of this kind has the advantage that, during the drying of the oral thin film, at the point at which the saturation concentration of the at least one pharmaceutically active agent is exceeded in the oral thin film, this at least one pharmaceutically active agent does not crystallise in an uncontrolled and inhomogeneous manner, since the at least one material which serves as crystal nucleus for the at least one pharmaceutically active agent causes a homogeneous and controlled crystallisation of the at least one pharmaceutically active agent in the oral thin film.

Crystal nuclei or cores are finely dispersed or macroscopic, solid particles in a fluid phase which facilitate crystallisation, i.e. the formation of crystals.

The concentration of the at least one pharmaceutically active agent in the oral thin film is greater than the saturation concentration of the at least one pharmaceutically active agent in the oral thin film. The saturation is understood here in the solid-in-solid physical state. In other words, the concentration of the solid active agent in the dried, solid oral thin film.

The saturation concentration is considered to mean the concentration of the at least one pharmaceutically active agent in the oral thin film at which the active agent recrystallises independently once the mixture has been spread. The recrystallisation can occur spontaneously following the spreading. It is known to a person skilled in the art, however, that such a recrystallisation can also occur in a time-delayed manner following the spreading.

The oral thin film according to the invention is preferably characterised in that the material which serves as crystal nucleus for the at least one pharmaceutically active agent is contained in the oral thin film in an amount of 0.01 to 20 wt. %, preferably 0.01 to 10 wt. %, especially preferably 0.01 to 5 wt. %, in relation to the total weight of the oral thin film.

If the material which serves as crystal nucleus for the at least one pharmaceutically active agent is present in smaller amounts, insufficient crystal nuclei will thus be present for ensuring homogeneous crystallisation.

If the material which serves as crystal nucleus for the at least one pharmaceutically active agent is present in larger amounts, the film properties might be influenced disadvantageously.

The oral thin film according to the invention is preferably characterised in that the material which serves as crystal nucleus for the at least one pharmaceutically active agent comprises small particles which are insoluble in the medium of the production compound.

In this context, "small" means a mean particle size of 5 to 100 μm, preferably 20 to 50 μm, wherein the mean particle size is deduced from the product data sheets of the respective manufacturers as valid on the filing date.

The oral thin film according to the invention is also especially preferably characterised in that the material which serves as crystal nucleus for the at least one pharmaceutically active agent comprises amorphous, pyrogenic silicon dioxide.

Amorphous pyrogenic silicon dioxide ($SiO_2$), also referred to as amorphous pyrogenic silica (or fumed silica), is a synthetically produced, colloidal silicon dioxide. It consists substantially completely of amorphous silicon dioxide particles which are aggregated to form larger units.

Suitable amorphous pyrogenic silicon dioxides are known for example from the range having the trade name "Aerosil®" by Evonik.

In addition, $TiO_2$, iron oxide(s), aluminium trioxide and/ or magnesium stearate are suitable as materials which serve as crystal nuclei for the at least one pharmaceutically active agent.

In a preferred embodiment the oral thin film according to the invention is characterised in that the at least one polymer comprises a water-soluble and/or water-swellable polymer.

Water-soluble/water-swellable polymers comprise chemically very different natural or synthetic polymers, the common feature of which is their solubility/swellability in water or aqueous media. A precondition is that these polymers have a number of hydrophilic groups sufficient for the water solubility/water swellability and are not crosslinked. The hydrophilic groups may be non-ionic, anionic, cationic and/or zwitterionic.

The at least one polymer in the oral thin film according to the invention is preferably selected from the group consisting of starch and starch derivatives, dextrans, cellulose derivatives, such as carboxymethyl cellulose, hydroxypropyl cellulose, hydroxyethyl cellulose, hydroxypropyl methylcellulose, hydroxypropyl ethyl cellulose, sodium carboxymethyl cellulose, ethyl or propyl cellulose, polyacrylic acids, polyacrylates, polyvinylpyrrolidones, polyvinyl alcohols, polyethylene oxide polymers, polyacrylamides, polyethylene glycols, gelatines, collagen, alginates, pectin, pullulan, tragacanth, chitosan, alginic acid, arabinogalactan, galactomannan, agar, agarose, carrageenan, natural gums, and mixtures thereof.

In a preferred embodiment the oral thin film according to the invention is characterised in that the at least one polymer is contained in the oral thin film in an amount of 30 to 80 wt. % in relation to the total weight of the oral thin film.

The at least one pharmaceutically active agent contained in the oral thin film according to the invention is not limited. Examples of suitable active agent classes include hypnotics, sedatives, antiepiletics, analeptics, psychoneurotropic drugs, neuro-muscle blockers, antspasmodics, antihistamines, antiallergics, cardiotonics, antiarrhythmics, diuretics, hypotensives, vasopressors, antidepressants, antitussives, expectorants, thyroid hormones, sexual hormones, antidiabetics, antitumour active agents, antibiotics, chemotherapeutics and narcotics.

The at least one pharmaceutically active agent in the oral thin film according to the invention especially preferably comprises ketamine and/or a pharmaceutically acceptable salt thereof, preferably ketamine.HCl.

Ketamine is understood to mean (S)-(±)-2-(2-chlorophenyl)-2-(methylamino)cyclohexan-1-one ((S) ketamine), (R)-(±)-2-(2-chlorophenyl)-2-(methylamino)cyclohexan-1-one ((R) ketamine), and the racemate (RS)-(±)-2-(2-chlorophenyl)-2-(methylamino)cyclohexan-1-one.

The at least one pharmaceutically active agent in the oral thin film according to the invention very especially preferably comprises (S) ketamine and/or a pharmaceutically acceptable salt thereof, preferably (S) ketamine.HCl.

The at least one pharmaceutically active agent in the oral thin film according to the invention preferably comprises adrenaline ((R)-4-[1-hydroxy-2-(methylamino)ethyl]benzene-1,2-diol), preferably in the form of hydrogen tartrate.

The oral thin film according to the invention is preferably characterised in that the oral thin film comprises at least one auxiliary substance selected from the group comprising colouring agents, flavourings, sweeteners, taste-masking agents, emulsifiers, enhancers, pH regulators, humectants, preservatives and/or antioxidants.

Each of these auxiliaries is preferably contained in the oral thin film in each case in an amount of approximately 0.1 to 10 wt. % in relation to the total weight of the oral thin film.

The oral thin film according to the invention is preferably characterised in that the mass per unit area of the oral thin film is approximately 50 to 300 $g/m^2$, preferably approximately 100 to 200 $g/m^2$.

The oral thin film according to the invention especially preferably comprises (S) ketamine, preferably in an amount of 40 to 50 wt. % in relation to the total weight of the oral thin film, at least one hydroxypropyl methylcellulose, preferably in an amount of 10 to 50 wt. % in relation to the total weight of the oral thin film, and a pyrogenic amorphous silicon dioxide, preferably in an amount of 0.1 to 2 wt. % in relation to the total weight of the oral thin film.

The present invention also relates to a method for producing the oral thin film described above.

The method comprises the steps of
a) producing a suspension or solution, comprising the at least one polymer, the at least one pharmaceutically active agent and the material which serves as crystal nucleus for the at least one pharmaceutically active agent, and
b) spreading and drying the suspension or solution obtained in step a) in order to obtain a thin film, preferably with a mass per unit area of approximately 50 to 300 $g/m^2$.

The amount of the at least one pharmaceutically active agent present in the suspension or solution in step a) is preferably such that the active agent in the oral thin film obtained following the drying in step b) is present in a concentration that is greater than the saturation concentration of the at least one pharmaceutically active agent in the oral thin film obtained following the drying in step b).

The solvent used in method step a) is preferably an aqueous solvent.

The suspension or solution in method step a) can preferably be heated.

It is consequently especially preferred if the at least one pharmaceutically active agent in step a) is present substantially completely dissolved.

The term "substantially completely" is understood here to mean that at least 85%, preferably at least 90%, very especially preferably at least 95%, and most preferably at least 99% of the at least one pharmaceutically active agent is present in dissolved form.

It is also preferred that the at least one pharmaceutically active agent, during the drying in step b) crystallises substantially until below the saturation limit (saturation concentration solid-in-solid). The at least one pharmaceutically active agent is especially preferably substantially completely and homogeneously distributed in crystalline form in the oral thin film.

The term "substantially" is understood here to mean that at least 85%, preferably at least 90%, very especially preferably at least 95%, and most preferably at least 99% of the at least one pharmaceutically active agent is present in crystalline form, preferably homogeneously distributed, in the oral thin film.

The present invention furthermore relates to an oral thin film obtainable by the method described above.

In addition, the present invention relates to an oral thin film, as described above or obtainable by the above-described method, as a medicament.

The present invention additionally relates to an oral thin film, as described above or obtainable by the above-described method, as a medicament for use in the treatment of depressions, especially to reduce the risk of suicide and/or for use as a general anaesthetic, preferably to initiate and carry out general anaesthesia, or as a supplement in the case of local anaesthesia and/or as an analgesic.

The preferred embodiments described above for the thin film according to the invention are also applicable for the method according to the invention, the oral thin film obtained thereby, and use of said oral thin film as a medicament.

The invention will be described in greater detail hereinafter on the basis of non-limiting examples.

EXAMPLES

Example 1

|  |  | Proportion [wt. %] | |
| --- | --- | --- | --- |
| Ingredient | Function |  | Comparative example |
| (S) ketamine | Active agent | 41.0 | 41.0 |
| HPMC 603 (3 mPas)[1] | Polymer | 39.0 | 39.5 |
| HPMC 60SH50 (50 mPas)[1] | Polymer | 10.0 | 10.0 |
| Glycerol | Humectant | 3.5 | 3.5 |
| Sucralose | Taste corrector | 1.0 | 1.0 |
| Saccharin Na | Taste corrector | 2.0 | 2.0 |
| Cherry Flavour EU | Taste corrector | 3.0 | 3.0 |
| Aerosil 200[2] | Crystal nucleus | 0.5 | — |
| Water | Residual moisture | 8 | 8 |

[1]Hydroxypropyl methylcelluloses with different viscosities, wherein these have a viscosity of approximately 3 or approximately 50 mPas (measured by USP monograph <911> method 1, from 2012).
[2]Pyrogenic amorphous $SiO_2$ from Evonik.

Figure 1:
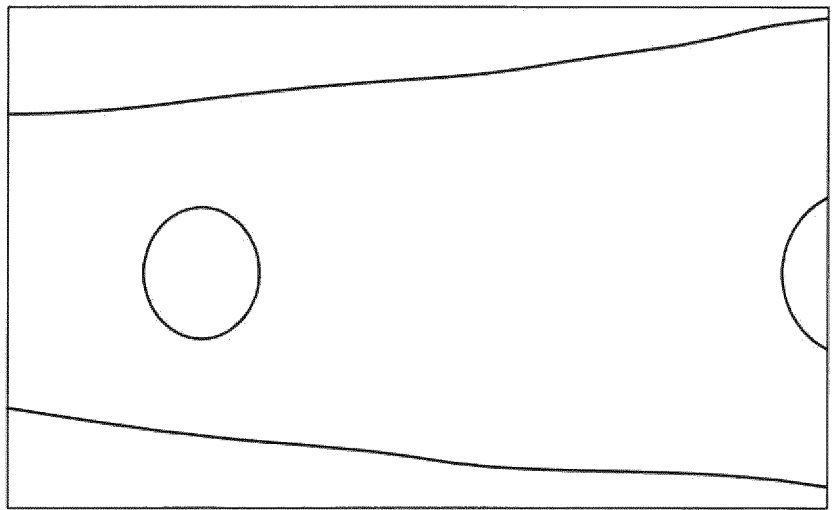
FIG. 1 shows a thin film according to the invention in accordance with the formulation specified in Table 1, directly after the drying.

The oral thin film according to the invention has a homogeneous appearance. The active agent is present in crystalline form, homogeneously distributed, in the oral thin film (see FIG. 1).

Figure 2:
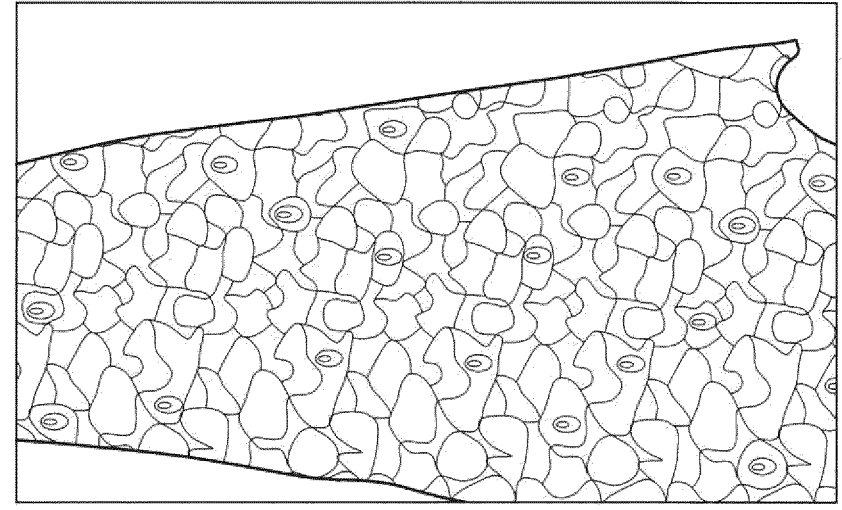
FIG. 2 shows a thin film according to the comparative example specified in Table 1, after the drying.

The oral thin film according to the formulation of the comparative example has an extremely inhomogeneous appearance. The active agent is inhomogeneously crystallised so that the oral thin film has many fracture lines (see FIG. 2).

The invention claimed is:

1. An oral thin film comprising at least one polymer and at least one pharmaceutically active agent, wherein the concentration of the at least one pharmaceutically active agent in the oral thin film is greater than the saturation concentration of the at least one pharmaceutically active agent in the oral thin film, characterised in that the oral thin film comprises at least one material which serves as crystal nucleus for the at least one pharmaceutically active agent, wherein the at least one pharmaceutically active agent is substantially completely and homogeneously distributed in crystalline form in the oral thin film.

2. The oral thin film according to claim 1, characterised in that the material which serves as crystal nucleus for the at least one pharmaceutically active agent is contained in the oral thin film in an amount of 0.01 to 20 wt. % in relation to the total weight of the oral thin film.

3. The oral thin film according to claim 1, characterised in that the material which serves as crystal nucleus for the at least one pharmaceutically active agent comprises amorphous, pyrogenic silicon dioxide.

4. The oral thin film according to claim 1, characterised in that the at least one polymer comprises a water-soluble and/or water-swellable polymer.

5. The oral thin film according to claim 1, characterised in that the at least one polymer is selected from the group consisting of starch and starch derivatives, dextrans, cellulose derivatives, such as carboxymethyl cellulose, hydroxypropyl cellulose, hydroxyethyl cellulose, hydroxypropyl methylcellulose, hydroxypropyl ethyl cellulose, sodium carboxymethyl cellulose, ethyl or propyl cellulose, polyacrylic acids, polyacrylates, polyvinylpyrrolidones, polyvinyl alcohols, polyethylene oxide polymers, polyacrylamides, polyethylene glycols, gelatines, collagen, alginates, pectin, pullulan, tragacanth, chitosan, alginic acid, arabinogalactan, galactomannan, agar, agarose, carrageenan, natural gums, and mixtures thereof.

6. The oral thin film according to claim 1, characterised in that the at least one polymer is contained in the oral thin film in an amount of 30 to 80 wt. % in relation to the total weight of the oral thin film.

7. The oral thin film according to claim 1, characterised in that the pharmaceutically active agent is selected from the group consisting of hypnotics, sedatives, antiepiletics, analeptics, psychoneurotropic drugs, neuro-muscle blockers, antspasmodics, antihistamines, antiallergics, cardiotonics, antiarrhythmics, diuretics, hypotensives, vasopressors, antidepressants, antitussives, expectorants, thyroid hormones, sexual hormones, antidiabetics, antitumour active agents, antibiotics, chemotherapeutics and narcotics.

8. The oral thin film according to claim 1, characterised in that the at least one pharmaceutically active agent comprises ketamine or a pharmaceutically acceptable salt thereof.

9. The oral thin film according to claim 1, characterised in that the oral thin film further comprises at least one auxiliary selected from the group comprising colouring agents, flavourings, sweeteners, taste-masking agents, emulsifiers, pH regulators, humectants, preservatives and/or antioxidants.

10. The oral thin film according to claim 1, characterised in that the at least one pharmaceutically active agent comprises(S) ketamine or a pharmaceutically acceptable salt thereof.

11. The oral thin film according to claim 1 wherein the pharmaceutically active agent comprises(S) ketamine in an amount of 40 to 50 wt. % in relation to the total weight of the oral thin film, the oral thin film includes hydroxypropyl methylcellulose in an amount of 10 to 50 wt. % in relation to the total weight of the oral thin film, and the at least one material comprises a pyrogenic amorphous silicon dioxide in an amount of 0.1 to 2 wt. % in relation to the total weight of the oral thin film.

12. A method for producing an oral thin film according to claim 1, comprising the steps of:
   a) producing a suspension or solution, comprising the at least one polymer, the at least one pharmaceutically active agent and the material which serves as crystal nucleus for the at least one pharmaceutically active agent, and
   b) spreading and drying the suspension or solution obtained in step a) in order to obtain a thin film.

13. The method according to claim 12, wherein the at least one pharmaceutically active agent in step a) is present substantially completely dissolved.

14. The method according to claim 12, wherein the at least one pharmaceutically active agent, during the drying in step b), crystallises until below the saturation limit.

15. An oral thin film obtainable by the method according to claim 12.

16. A method for delivering hypnotics, sedatives, antiepiletics, analeptics, psychoneurotropic drugs, neuro-muscle blockers, antspasmodics, antihistamines, antiallergics, cardiotonics, antiarrhythmics, diuretics, hypotensives, vasopressors, antidepressants, antitussives, expectorants, thyroid hormones, sexual hormones, antidiabetics, antitumour active agents, antibiotics, chemotherapeutics or narcotics to a patient, comprising administering an effective amount of a pharmaceutically active agent using the oral thin film according to claim 1.

17. A method for producing an oral thin film according to claim 1, comprising the steps of:

a) producing a suspension or solution, comprising the at least one polymer, the at least one pharmaceutically active agent and the material which serves as crystal nucleus for the at least one pharmaceutically active agent, and b) spreading and drying the suspension or solution obtained in step a) in order to obtain a thin film with a mass per unit area of approximately 50 to 300 g/m$^2$.

* * * * *